US005478328A

United States Patent [19]
Silverman et al.

[11] Patent Number: 5,478,328
[45] Date of Patent: Dec. 26, 1995

[54] METHODS OF MINIMIZING DISEASE TRANSMISSION BY USED HYPODERMIC NEEDLES, AND HYPODERMIC NEEDLES ADAPTED FOR CARRYING OUT THE METHOD

[76] Inventors: David G. Silverman; Sally A. Kniffin, both of 3 Meeker Hill Rd., Redding, Conn. 06896

[21] Appl. No.: 116,212

[22] Filed: Sep. 2, 1993

Related U.S. Application Data

[63] Continuation of Ser. No. 887,705, May 22, 1992, abandoned.

[51] Int. Cl.⁶ .................................................. A61M 5/32
[52] U.S. Cl. .......................... 604/272; 604/198; 604/110; 604/274; 604/263
[58] Field of Search ..................... 604/192, 263, 604/273, 274, 168, 414, 198, 28, 272, 278, 290, 49; 128/764, 919

[56] References Cited

U.S. PATENT DOCUMENTS

| | | | |
|---|---|---|---|
| 145,217 | 12/1873 | Leiter | 604/218 |
| 561,059 | 5/1896 | Mitchell et al. | 604/165 |
| 762,603 | 6/1904 | Witkowski | 604/241 |
| 1,526,595 | 2/1925 | Gillman | 128/764 |
| 2,097,039 | 10/1937 | Peterson . | |
| 2,410,991 | 11/1946 | Müller | 604/201 |
| 2,460,641 | 2/1949 | Kleiner . | |
| 2,607,347 | 8/1952 | Kleiner | 128/764 |
| 2,634,726 | 4/1953 | Hanson . | |
| 2,862,495 | 12/1958 | Gewecke . | |
| 3,181,336 | 5/1965 | Schofield et al. | 72/340 |
| 3,469,572 | 9/1969 | Nehring . | |
| 3,492,992 | 2/1970 | Kurtz . | |
| 3,494,352 | 2/1970 | Russo et al. . | |
| 3,509,880 | 5/1970 | Guttman | 604/272 |
| 3,882,849 | 3/1974 | Jamshidi | 128/753 |
| 3,906,932 | 9/1975 | Ayres | 128/764 |
| 4,058,121 | 11/1977 | Choksi et al. . | |
| 4,121,585 | 10/1978 | Becker, Jr. | 604/214.4 |
| 4,155,350 | 5/1979 | Percarpio | 128/764 |
| 4,190,048 | 2/1980 | Sampson | 604/218 |
| 4,232,669 | 11/1980 | Nitshke | 604/218 |
| 4,392,499 | 7/1983 | Towse | 128/764 |
| 4,411,657 | 10/1983 | Galindo | 604/274 |
| 4,413,993 | 11/1983 | Guttman | 604/274 |
| 4,419,098 | 12/1983 | Bennett | 604/263 |
| 4,516,967 | 5/1985 | Kopfer | 604/87 |

(List continued on next page.)

FOREIGN PATENT DOCUMENTS

| | | |
|---|---|---|
| 1196601 | 11/1959 | France . |
| 0446818 | 6/1927 | Germany . |
| 3020926 | 12/1981 | Germany . |
| 3026657 | 2/1982 | Germany ................................ 604/274 |

OTHER PUBLICATIONS

Hart, Jr., et al. Pencil–Point Needle in Prevention of Postspinal Headache. JAMA 147:657–8, 1951.

Sprotte, G., et al. Eine "atramatische" Universalkanüle füreinzeitige Regionalanaesthesien.—Reg Anaesthesie 10:104–108, 1987.

Kleen–Needle System, Brochure, TN State Hospital Supply Corp.

*Primary Examiner*—C. Fred Rosenbaum
*Assistant Examiner*—V. Alexander
*Attorney, Agent, or Firm*—Ostrolenk, Faber, Gerb & Soffen

[57] ABSTRACT

A needle, related attachments, and methods of constructing and using the same, for reducing the risk of infection from material in a used hypodermic needle. The needle is formed with a solid tip having no orifice, at a distal end of the needle. At least one longitudinal bore is formed in the needle which terminates proximal to the needle tip. At least one outlet orifice is formed in communication with the bore, for passage of all material into or out of the needle, the outlet orifice being located at a lateral position spaced back from the solid tip, thereby reducing the risk that an individual who contacts the tip of the needle will contact material retained in the needle.

4 Claims, 15 Drawing Sheets

U.S. PATENT DOCUMENTS

| | | | |
|---|---|---|---|
| 4,537,593 | 8/1985 | Alchas | 604/411 |
| 4,710,180 | 12/1987 | Johnson | 604/239 |
| 4,730,624 | 3/1988 | Waters | 128/764 |
| 4,767,407 | 8/1988 | Foran | 604/164 |
| 4,795,446 | 1/1989 | Fecht | 604/264 |
| 4,808,157 | 2/1989 | Coombs | 604/44 |
| 4,834,716 | 5/1989 | Ogle, II | 604/192 |
| 4,836,373 | 6/1989 | Goldman | 206/366 |
| 4,846,809 | 7/1989 | Sims | 604/198 |
| 4,894,052 | 1/1990 | Crawford | 604/53 |
| 5,053,018 | 10/1991 | Talonn et al. | 604/198 |

INTRADERMAL

SHORT

REGULAR

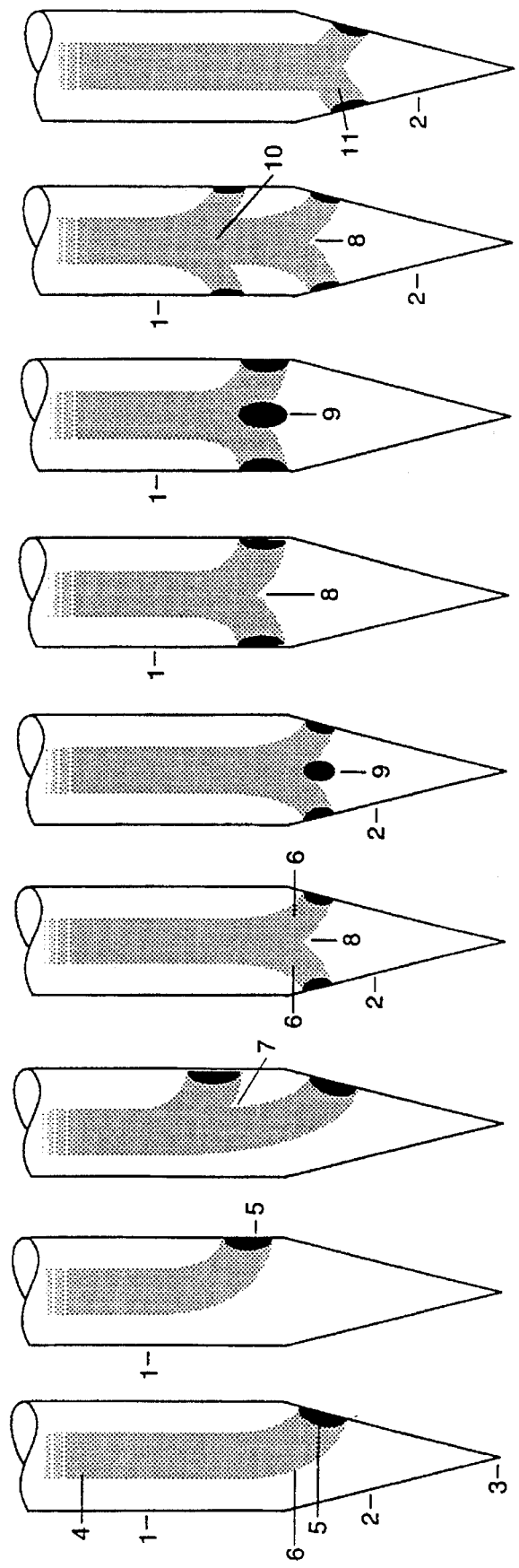

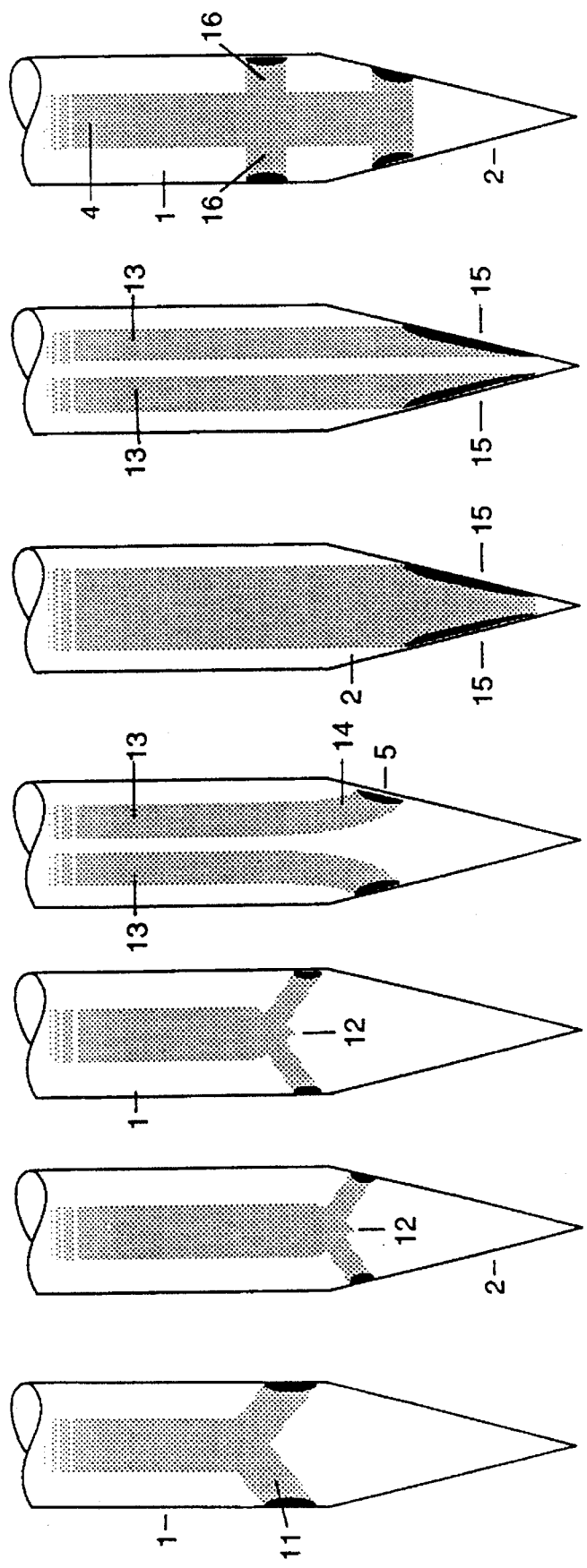

STANDARD TUOHY NEEDLE

SHARP TIP

BLUNT TIP

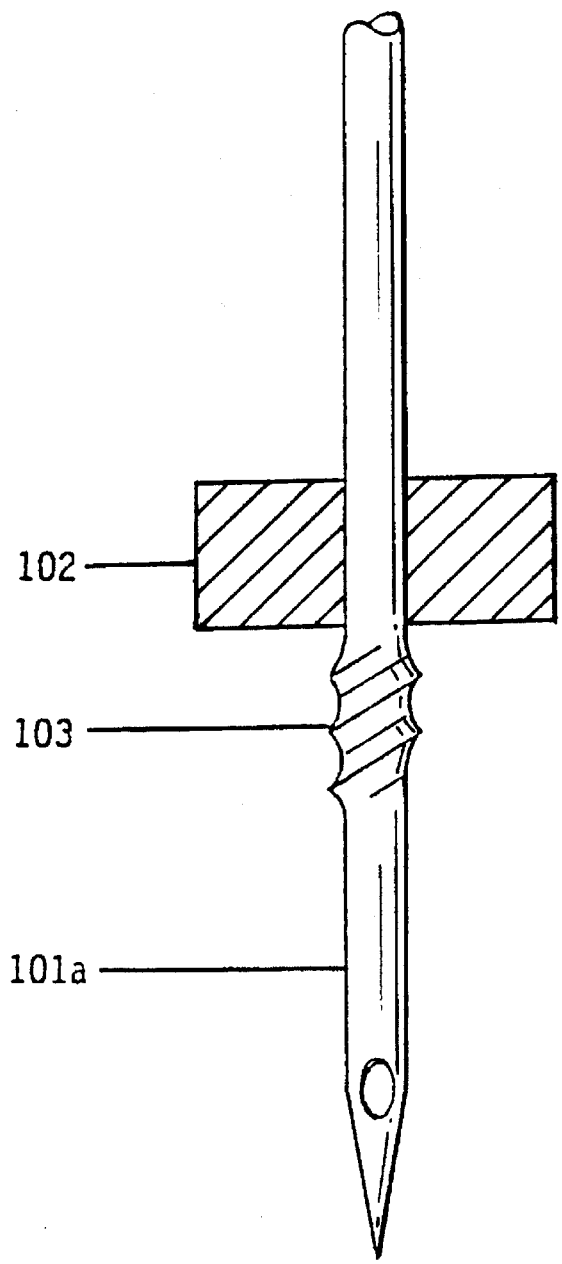
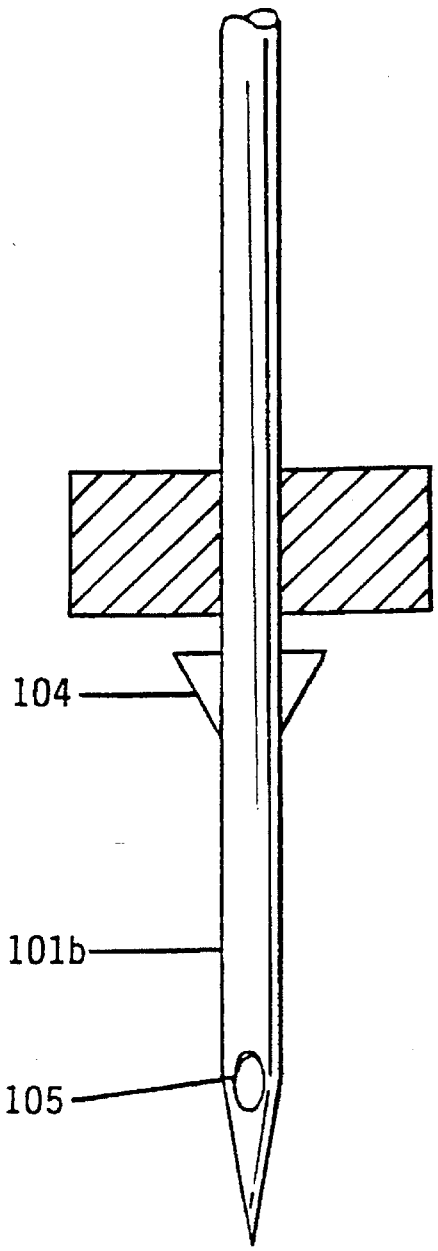
FIG. 8 a
FIG. 8 b

METHODS OF MINIMIZING DISEASE TRANSMISSION BY USED HYPODERMIC NEEDLES, AND HYPODERMIC NEEDLES ADAPTED FOR CARRYING OUT THE METHOD

This is a Continuation of Application Ser. No. 07/887,705 filed on May 22, 1993 now abandoned.

BACKGROUND OF THE INVENTION

The invention relates to methods of minimizing disease transmission by used hypodermic needles, and hypodermic needles adapted for carrying out the methods.

Known hypodermic needles typically have (a) a sharp point to facilitate penetration of the skin, a bottle top or an injection port; and (b) an open tip to allow for injection and withdrawal of fluid. Typically such needles have cutting points, formed by a beveled cut with an opening created at the junction of the beveled edge and the needle bore.

FIGS. 1a–1c respectively show intradermal, short, and regular needle points, the basic types currently available from Becton-Dickinson, the largest manufacturer.

Unfortunately, these features pose a threat to anyone who comes into contact with a used needle. The sharp point increases the likelihood of skin puncture. The open tip can house infected fluid or tissue and thereby transmit disease to an individual who subsequently is exposed to the needle.

These features have the most significant consequences for individuals exposed to human products in environments where hepatitis and AIDS are of paramount concern. Transmission of malaria, treponema pallidum, Rocky Mountain spotted fever, tuberculosis, toxoplasmosis, blastomycosis, cryptococcosis, brucellosis and leptospirosis by infected needles also has been reported; hence there also is concern among individuals working in veterinary practices and research laboratories. These risks can be extended to the general public through improper needle disposal, illicit use of needles, etc.

The multiple sources of needle stick injury indicate that there is no single remedy. In a recent study, Jagger et al. (N Engl J Med 319:284–288, 1988) noted that one third of the 326 needle-stick injuries reported in a university hospital in a ten-month period were related to recapping. Needles inserted into intravenous tubings had the second highest rate of injury as a result of intentional and inadvertent detachment. The authors concluded that:

Each device that causes such
injuries must be modified according
to its specific use and handling
requirements . . . . To provide the
greatest benefit, the safety feature
should be an integral part of the
device and not an accessory to be
used in combination with a hazardous
item. In this way, it is certain to
be available precisely when and where
it is needed. Moreover, the safety
feature should be in effect before
disassembly and should remain in
effect after disposal, thus
protecting the trash handler as well
as the user. Finally, safety features
should be as simple as possible and
should require little or no training
to use effectively. [N. Eng. J. Med.
319:284–288, 1988.]

The problem was addressed in Newsweek, in an article entitled "A Very Risky Business" (Nov. 20, 1989). In response to this article, a reader wrote:

Try to gown, glove, double boot
. . . while a patient is extubating
himself from a ventilator, or pulling
out his i.v. lines, or is in cardiac
arrest. The reason adequate
precautions receive such a low
compliance is not from lack of a
desire to implement them but because
in a few precious moments one must
act quickly to protect the patient
from known harm, not oneself from
potential harm. [Makar, E. V., Letter
to Editor, December 18, 1989.]

Such scenarios contribute to more than 800,000 accidental needle sticks each year.

Recent attempts to address the problems associated with recapping have included:

a) incorporating a plastic casing that is advanced over the needle tip automatically as a catheter is slipped over a needle to be placed in a vessel (Critikon, Inc. 1990).

b) incorporating a plastic casing which is manually advanced from around the syringe barrel to beyond the needle tip such that recapping is less likely to be associated with inadvertent skin puncture (Becton-Dickinson, Inc. 1990).

c) recapping needles in a special adaptor which is secured to a table top rather than in a traditional cap which is held in one's hand (Goldman, U.S. Pat. No. 4,836,373).

d) providing guidance grooves in the cap to facilitate safe needle entry (Bennett, U.S. Pat. No. 4,419,098).

The disclosures of these references and all other prior art information mentioned herein are expressly incorporated by reference.

Certainly, the aforementioned devices might provide added safety. However, they are not foolproof. In addition, in many cases, they entail the use of far more plastic (with increased cost of manufacture and environmentally safe disposal), are more bulky than traditional devices, entail modifications of one's usual practices, may not be adaptable to all sizes of needles and syringes, and may not be universally applicable to the varied settings where needle sticks commonly occur.

In many settings, one tries to avoid the use of needles altogether when adding medications or supplemental fluids to an already existing intravenous line (as would be the case for all intraoperative patients and many other hospitalized patients). This commonly is accomplished by adding stopcocks to the intravenous tubing. However, typical stopcocks have certain limitations: (1) they generally can allow flow through either the main line or the sideport, but not through both simultaneously; (2) when the protective covering, syringe or tubing is removed from a port of the stopcock, this port may no longer be sterile and hence is a potential source of patient contamination; and (3) most intravenous tubing does not come with stopcocks in place (cost, bulkiness, risk of disconnect with leakage or blood loss, risk of patient contamination).

These limitations have led to the design of systems which entail modifying the male and female connectors such that the cannula pierces the diaphragm without the use of a needle (InterLink IV Access System, Baxter Healthcare Corp., 1990). Limitations of such modifications include: need to modify one's practices to use bulkier setups, increased cost, and need for increased use and disposal of plastic. Furthermore, the use of this system requires modification or replacement of existing setups, so that a matched cannula and diaphragm will always be available.

As a compromise, systems have been designed with plastic casing which extends around and beyond the needle shaft and tip. This fits into a matched receptor at the penetrable diaphragm of a bottle, tubing, etc. (Ogle, U.S. Pat. No. 4,834,716 produced as Stick-Gard Safety Needle by International Medical Systems, Limited 1990). These have not gained widespread acceptance because of many of the aforementioned limitations. Furthermore, these setups are not fool-proof, in that one can still contact a contaminated needle.

We conclude that needles probably are here to stay. While healthcare workers are eager to see the risks associated with needles eliminated, they also would prefer not to markedly change their practices. Changes in themselves may be associated with risks, in addition to increased cost and potential compromises in patient care. Furthermore, there are settings where the use of needles appears to be unavoidable, e.g., injections, blood withdrawal, and intravascular catheter insertion.

Thus, a major priority should be a method of providing needles so that they can be handled more safely. Even though a needle stick cannot totally be avoided, we believe that the consequences of such a stick can be decreased markedly if a needle with one or more recessed orifices on its shaft and/or taper is employed. In addition to the needles of the present disclosure themselves being inherently safer, they offer the additional advantage of facilitating the use of such safety features as the protective sheaths and caps described herein.

To date, all reported transmissions of AIDS via puncture wounds to health care workers have resulted from puncture with a hollow bore device such as a traditional hypodermic needle or a broken glass tube. These present a sizeable inoculum which may be avoided with the solid-tip needles described herein. Although solid-tip needles are commercially available from many manufacturers for use in spinal myelography and soft tissue biopsy, and perineural injections, as shown in FIG. 2, the art has recognized neither the methods nor the apparatus disclosed herein, nor their advantages.

A typical needle includes four integral elements: a proximal "hub" for fluidic attachment to a syringe or intravenous tubing; a straight tubular "shaft" which has a substantially uniform cross-section; a conical or tapered portion at the distal end of the straight tubular shaft portion (herein called "taper"); and a distal end or "tip". In addition, hypodermic needles have a removable cap which fits around the tip and shaft to removably frictionally engage the hub. None of these features, including the cap, increases user safety during needle use. Because it typically entails placing one's hand in front of the needle tip, the capping procedure may be so risky that many experts recommend that it not be performed (and that exposed needles be transported to containers for sharp disposal).

In preliminary evaluations at the Redding Ridge Veterinary Clinic (home veterinary office of Sally A. Kniffin VMD), we have addressed the types of needle usage for which a sharp point, an open tip, and/or an exposed tip are needed. These issues are addressed in Table 1. Summarizing Table 1, a sharp point would be required to pierce the skin or a blood vessel, but not necessarily to pierce a penetrable diaphragm. An open tip might be desirable for an intramuscular injection. Otherwise (and perhaps even in the case of intramuscular injection) a recessed side opening would be sufficient.

We also have assessed whether a retractable sheath or retractable cap could be employed in these settings. Such modifications are being introduced in the present disclosure for use with our inventive series of needles. Consistent with our aim, these modifications are designed to increase user safety. Their introduction is made practical by the inventive needles, which have solid tips and therefore avoid coring.

Prior solid tip needles with recessed orifices are known, as set out below. However, the methods and series of needles disclosed herein, as well as needle/catheter combinations, means of securement, protective sheaths and retractable needle caps, have features specifically adapted for minimizing disease transmission by used hypodermic needles. More particularly, we have optimized the shaft, taper and tip of the needle, modified overlying catheters, and introduced means of covering with specially designed sheaths and caps. The disclosed methods provide unprecedented protection for the healthcare worker and a family of inventive needles which carry out the disclosed methods.

The following patent references (U.S. unless noted otherwise) disclose background types of recessed-orifice devices: Leiter U.S. Pat. No. 145,217; Mitchell and Gillespie U.S. Pat. No. 561,059; Gillman U.S. Pat. No. 1,526,595; Weyl 446,818 (German);Peterson U.S. Pat. No. 2,097,039; Hanson U.S. Pat. No. 2,634,726; Gewecke U.S. Pat. No. 2,862,495; Morgan 1,196,601 (French); Schofield U.S. Pat. No. 3,181,336; GuttmanU.S. Pat. No. 3,509,880; Jamshidi U.S. Pat. No. 3,882,849; Choksi U.S. Pat. No. 4,058,121; Sampson U.S. Pat. No. 4,190,048; Galindo U.S. Pat. No. 4,411,657; Guttman U.S. Pat. No. 4,413,993; Johnson U.S. Pat. No. 4,710,180; Sprotte 3,020,926 (German); Foran U.S. Pat. No. 4,767,407. Hanson (U.S. Pat. No. 2,634,726) discloses a needle with a chisel-like point and a single recessed orifice which opens obliquely on the side of the shaft ipsilateral of the convex side of the needle point and is said to minimize the likelihood of clogging the needle and reinjecting a cork or rubber core into a patient. These references disclose one or more of the following objectives: (1) to avoid coring of a rubber diaphragm by an open-bevel needle; (2) to minimize trauma to a patient's tissues; (3) to decrease the likelihood of intraneural injections; (4) to provide an additional orifice to allow venting; and (5) to provide a special needle hub. None discloses the specific features and methods of this invention which increase user safety.

Since 1980, there have been several adaptations and modifications of recessed-orifice types of design. In 1983, Galindo (U.S. Pat. No. 4,411,657) disclosed a needle with a solid tapered tip and recessed orifice introduced to decrease nerve trauma during injection of local anesthetic. In that same year, Guttman (U.S. Pat. No. 4,413,993) claimed his recessed-orifice needle for minimizing infiltration from the cannulated vessel during intravenous infusion of fluid (even if the tip of the needle extended beyond the back wall of the vessel). In 1985, Alchas (U.S. Pat. No. 4,537,593) introduced a recessed-orifice needle with an overlying sleeve to allow venting during transfer of liquid to or from a container. In 1987, Johnson (U.S. Pat. No. 4,710,180) described a blunt-tipped cannula with multiple recessed orifices for injecting fat cells into the skin after an incision was made to allow cannula insertion. In 1987, Sprotte (German 3,020, 926) introduced a modified recessed-orifice needle for regional anesthesia with improved flow characteristics and a lesser incidence of dural tear and postspinal headache.

None of these references discloses features or methods which increase user safety, as will be detailed in the ensuing description.

SUMMARY OF THE INVENTION

A central object of the invention is to provide methods to reduce the risk of transmitting disease to individuals exposed to used hypodermic needles.

A further object is to provide needle modifications, and combinations thereof, which increase user safety.

Our ultimate goal is to provide needles which meet commonly encountered needs while minimizing the risk of contacting a conventional open-bevel point.

Particular aspects of the invention include:

a) locating and designing the orifice(s) to decrease the likelihood that inadvertent needle stick would result in injection of an inoculum.

b) configuring passages between the axial channel and the orifice(s) to promote drainage of intraluminal fluid.

c) tailoring the taper configuration and degree of tip sharpness to maximize user safety while satisfying the requirements of a given usage.

d) adapting these modifications to needle/catheter assemblies for arterial and venous cannulation.

The aforementioned features are suitable, alone or in combination, for use with other new features of the present disclosure that increase utility as well as safety, such as:

e) providing means to secure the inventive needles in place such that the above-mentioned orifices are located properly for aspiration and injection and do not become dislodged.

f) providing means for covering the recessed orifices of the inventive needles with a retractable sheath that permits the orifices to be open when in use and covered subsequent to use (without concern about potential coring by an open-bevel tip).

g) providing means for capping the needle with a retractable cap that has a penetrable diaphragm (since the solid tip of the inventive needles will not pose the risk of coring that is inherent in open-bevel designs).

While the aforementioned features may be used alone, they also are well-suited to improve the safety and efficiency of other commercially available products. For example: (1) The present invention's solid tip, recessed orifices and means for covering them may further increase the safety of needles which are encased in a plastic housing since the commercial configuration does not prevent the user's finger from contacting the needle tip (e.g., Stick-Gard Safety Needle, IMS, Ltd). (2) If used with special diaphragms that are penetrable by blunt cannulae (e.g., Interlink IV Access System, Baxter Healthcare Corp.), blunt-tipped needles of the present inventive series may offer greater flexibility with respect to retaining the ability to puncture bottle tops and other penetrable sites. Use of the inventive needles could avoid the need to interchange needles and cannulae and would reduce the risk of breakage.

Other objects, features and advantages of the present invention will become apparent from the following description of the invention which refers to the accompanying drawings.

BRIEF DESCRIPTION OF THE DRAWINGS

FIGS. 3a–3p are schematic diagrams showing sixteen needles according to embodiments of the invention, all including a solid tip, a typical tapered region, and recessed orifice(s) along the shaft and/or the tapered region of the needle, some of the embodiments including a branched lumen and/or a well in the needle.

FIG. 5a showing a Huber epidural needle, FIG. 5b showing a Hustead epidural needle, and FIG. 5c showing several sharp and blunt Tuohy epidural needles.

FIGS. 8a and 8b show respective combinations of a recessed-orifice needle and a diaphragm, the needle being maintained in position by threaded frictional engagement and a radially extending flange, respectively.

DETAILED DESCRIPTION OF EMBODIMENTS OF THE INVENTION

I. NEEDLES

Figure 1A:
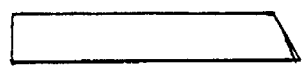
FIGS. 1a–1c illustrate standard types of open-tip bevels ("intradermal," "short," and "regular") that are available in conventional hypodermic needles, as illustrated in the Becton-Dickinson catalogue.
Figure 1B:
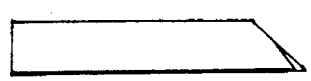
Figure 1C:
Figure 2A:
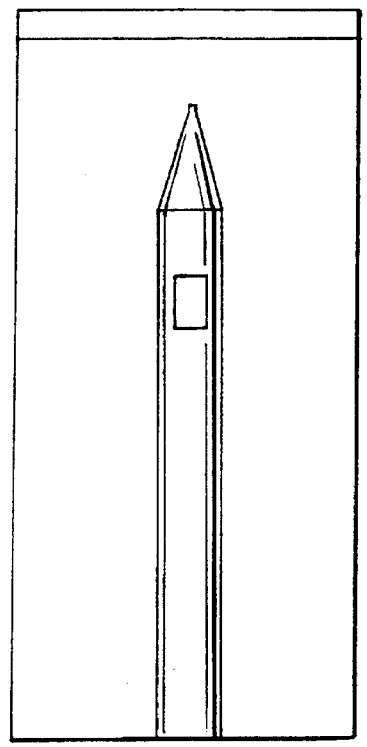
FIGS. 2a–2c show respectively a Whitacre-type spinal needle, a CHYNN myelography needle, and a Dos Santos lumbar aortography needle, as they appear in commercial catalogues.
Figure 2B:
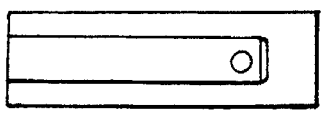
Figure 2C:
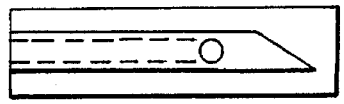

According to various embodiments of the invention, needles have orifices located and configured to minimize the likelihood of disease transmission. The needles according to these embodiments have a solid tip and one or more recessed orifices. The long axis of the needle contains a hollow tubular channel (or throughbore) extending from the proximal hub end (where a syringe or tubing would be attached in fluidic communication) to one or more orifices located at the distal end (near the solid tip). The orifices may be located at various distances from the needle tip. The hub may be marked to delineate orifice orientation. The channel may be midline or offset. The shaft may be thick-walled or thin-walled. The taper may be symmetrical or biased. The tip may be sharp or blunt.

Known needles with recessed orifices have not gained widespread use for routine hypodermic applications. They have been designed to meet certain procedural needs without involving any method or ability to improve user safety. The methods and the needles according to embodiments of the present invention specifically address and achieve user safety, among other goals. The disclosed needles, catheters, sheaths, and caps are adapted for use in carrying out the methods of this invention for increased user safety.

A. SPECIALLY CONFIGURED RECESSED ORIFICE(S)

FIGS. 3a–3p show several examples of needles according to the invention. The needles generally include a shaft 1, a tapered region 2, a solid tip 3, a tubular channel 4, and at least one recessed orifice 5 which is recessed from the tip.

The orifices 5 of the present invention may be round, oval, angular or slitted. They may be chamfered to minimize tearing of tissues or penetrable diaphragms, and they may be fenestrated (covered with a screen or the like) to limit exposure of contaminants. They may be located on the taper and/or shaft, and may arise from the end of the tubular channel or emerge along the course of the channel. Their diameter may be greater than, less than, or equal to that of the main axial channel. In particular embodiments, orifices are located on the same side of the needle such that they will all drain if placed with that side down. Alternatively, in other embodiments, the orifices are spaced 180° from each other around the needle or have another suitable angular spacing to promote drainage regardless of the resting position of the needle. The presence of more than one orifice facilitates injection and aspiration; e.g., if a needle is being used to withdraw blood from a blood vessel, a single recessed orifice is more likely to be completely occluded by the vessel wall.

Particular attention is drawn to the oblique and/or curved course imparted to the passage between the main tubular channel 4 and each orifice 5 in many of the embodiments. This promotes drainage, thereby lessening the likelihood that a used needle would retain an inoculum. Such passages may be imparted by a number of methods or means, several of which are illustrated:

a) imparting a curve or angle at the distal end of the channel and curving the passage 6 through the wall of the needle. The orifice 5 may be located on the taper 2 (FIG. 3a) and/or shaft 1 (FIG. 3b), rather than at the tip 3. A branch 7 may provide two passages and orifices at different distances from the tip; one may be on the taper and the other on the shaft (FIG. 3c). The wall thickness on the side of the orifice 5 may be increased or decreased by offsetting the axial channel (FIG. 3c);

b) inserting a terminal or nonterminal fork in the channel. FIG. 3d shows a two-pronged terminal fork 8 which provides passages 6 to two orifices on the taper 2. FIG. 3e shows a multi-pronged terminal fork 9 which provides three orifices on the taper. FIG. 3f shows a two-pronged terminal fork 8 and FIG. 3g shows a three-pronged terminal fork 9 which provide branches to orifices on the shaft 1. FIG. 3h illustrates a nonterminal two-pronged fork 10 and a terminal two-pronged fork 8 which provide channels to orifices on the shaft 1 and taper 2;

c) angling a single straight passage or multiple passages 11 to orifice(s) on taper 2 (FIG. 3i) or shaft 1 (FIG. 3j);

d) providing a well 12 to allow drainage of intra-luminal fluid at the level of taper 2 (FIG. 3k) and/or shaft 1 (FIG. 3j); or e) running independent channels 13, each of which may contain a curve 14 or angle, to provide for passage to an orifice 5 (FIG. 3m).

The aforementioned description of oblique and curved passages should not be taken as to exclude other passage types. Several of the advantages of the recessed orifices still may be obtained even if one simplifies the manufacturing process by:

f) providing a channel which simply merges with the side(s) of the taper 2 to create opening(s) 15. The channel may be central (FIG. 3n) or it may be offset as illustrated for the two independent channels 13 in FIG. 3o. The distal end of a channel may be widened to increase the diameter of the opening(s); or g) providing a passage or passages 16 which extend perpendicular to the main axial channel 4 (FIG. 3p).

B. MODIFICATIONS OF THE TAPERED REGION AND POINT

In many embodiments, the taper is 2 to 10 mm in length. For simplicity of illustration, the taper shown in FIGS. 3a–3p consists of straight sides. It would be obvious to someone experienced in the art of needle construction that the sides of the taper alternatively could come to a point by such means as gently curving the sides to converge to a conical tip.

Figures 4A, 4B, 4C, 4D, 4E, 4F:
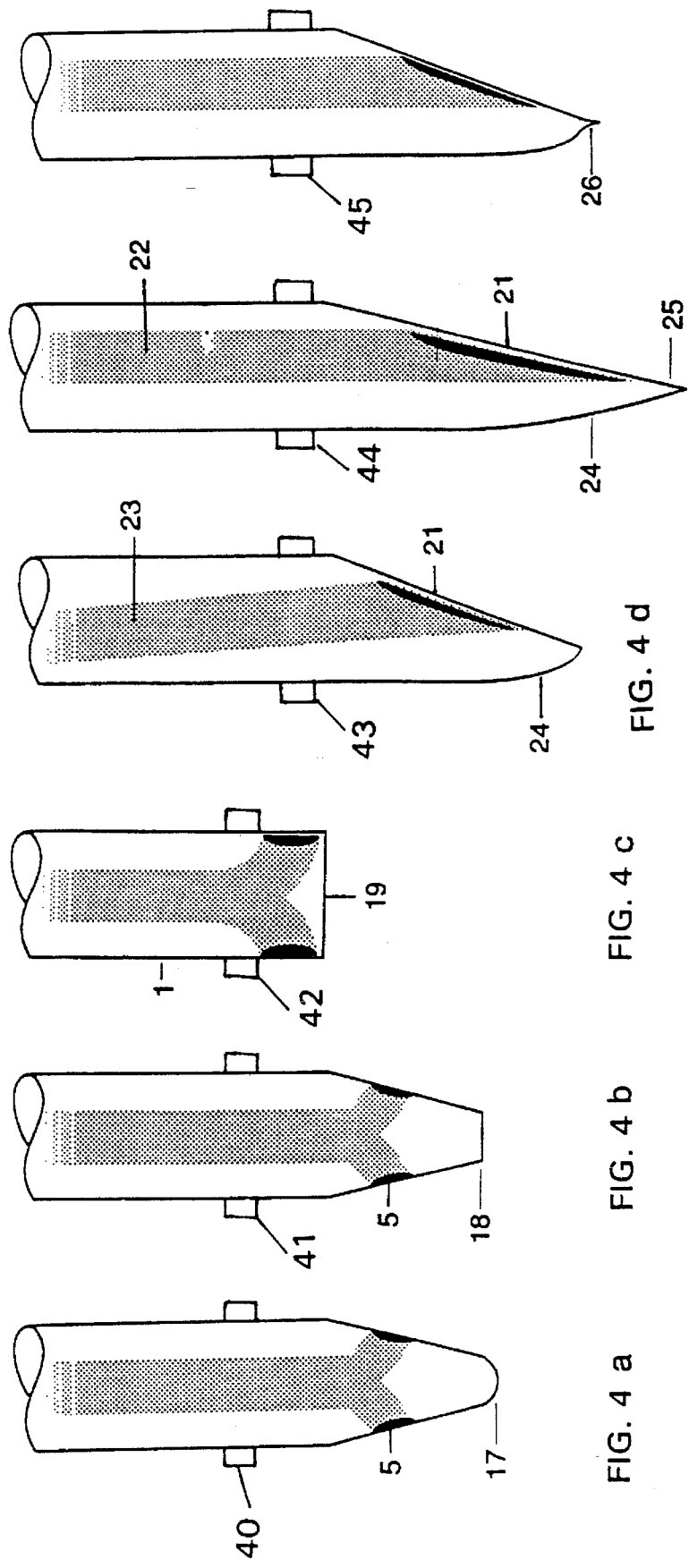
FIGS. 4a–4f are schematic diagrams showing six needles according to embodiments of the invention, all having a solid tip that has been modified to optimize desired penetration and maximize user safety.

FIGS. 4a–4g illustrate additional significant modifications of the tapered region and tip. Particular attention is drawn to how these variations provide the ability to select a needle taper and tip to meet particular needs while maintaining the orifice(s) recessed from the tip. Examples of how this may be accomplished include:

a) imparting a curve 17 to the end of the taper (FIG. 4a), imparting a flat "tip" 18 at the end of the taper (FIG. 4b) or replacing the taper and tip with the blunted end 19 of the needle shaft (FIG. 4c)——such means of blunting the end of the needle minimize the likelihood of a needle stick;

b) imparting a curve 24 to one side of the needle taper and slanting the other side 21 (FIGS. 4d–4f). FIG. 4d contains a straight channel 22 which remains parallel to the axis of the shaft to emerge on slanted side 21 of such a taper of variable length. FIG. 4e contains a straight channel that courses at a slant 23 to the axis of the shaft. Additionally, the channel may curve or contain an angle as shown in FIGS. 3a–3m and 3p;

c) imparting a sharper tip 26 to a curved tip needle (FIG. 4f), in order to facilitate skin and vessel penetration with a tip that is slender and sharp.

The ability to select a needle of appropriate sharpness increases the utility and value of the inventive series. Sharp tips may be utilized when indicated (Table 1). Alternatively, while the blunted tips illustrated in FIGS. 4a–4c would not be well-suited for penetration of a standard diaphragm, they would be well-suited for use with diaphragms that have been modified for easy penetration such as those designed for use with a blunt plastic cannula (Interlink, Baxter Healthcare Corp. 1990). In contrast to such cannulae, the inventive needles would maintain the strength and, depending on tip sharpness, could maintain the utility of needles. In contrast to prior needle art, the present disclosure constitutes the first clinical use of a blunt-tipped, recessed orifice needle which is designed for the uses described herein.

Figure 5A:
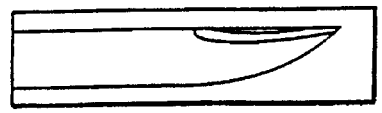
FIGS. 5a, 5b and 5c illustrate commercially available needles with curved tapered regions.
Figure 5B:
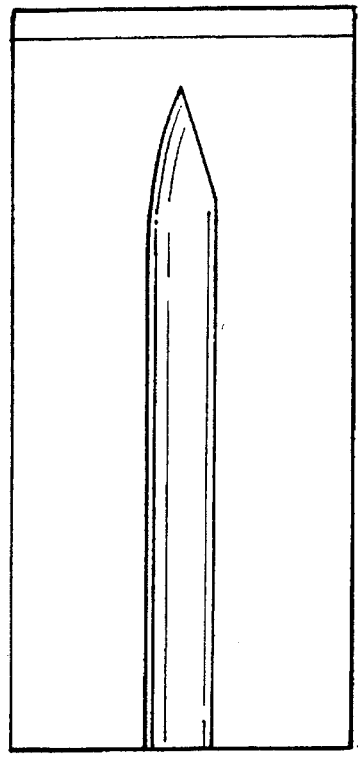
Figure 5C:
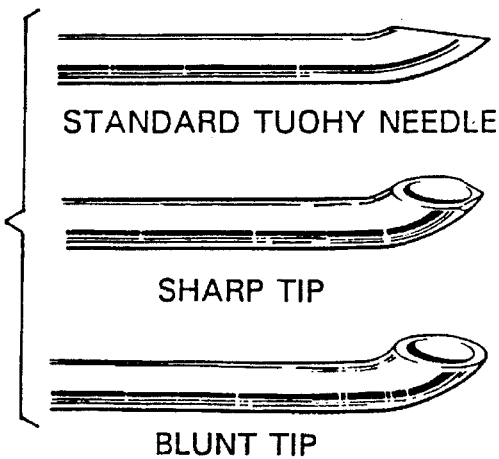

The curved tip (FIGS. 4d–4f) is well-suited for insertion into blood vessels and body cavities for injection, aspiration, and catheter insertion. While these needles share features in common with the Tuohy needle and modifications thereof illustrated in FIG. 5, the proposed uses and methods related to the inventive needles are very different and the features of the disclosed embodiments differ decidedly in order to achieve these aims. The Tuohy needle has a curved (Huber) tip for minimizing the likelihood of piercing the dura when inserting a needle for epidural anesthesia and for threading a catheter at a right angle or near-right angle for continuous epidural or continuous spinal anesthesia. In the construction of the present inventive needle, (1) the tip is sharpened for vessel penetration; (2) the shaft is much shorter (for example 1–1½ in. vs. 3½–4 in.) since the inventive needles need not penetrate the fat, muscles, and ligaments of the back; (3) the channel and orifices of the curved-tip embodiments of the present inventive needle are specially configured to face forward so as to avoid occlusion by the vessel wall and to impart forward (as opposed to right angle) direction to a through-the-needle catheter; and (4) the inventive needles are designed for use with matched over-the-needle catheters as well as through-the-needle catheters (as described below).

II. NEEDLES FOR INTRAVASCULAR CANNULATION AND MONITORING

Currently available hypodermic needles have been inserted intravascularly, alone or in combination with catheters or probes, for: (1) infusion and/or withdrawal directly through the needle; (2) localizing a blood vessel for subsequent passage of an "over-the-needle" plastic (Teflon) catheter; (3) localizing a blood vessel for subsequent passage of a "through-the-needle" catheter; and (4) entry into a blood vessel for passage of an intravascular monitoring probe or guidewire (for subsequent passage of an over-the-wire catheter). The typical procedure entails percutaneous insertion with the needle at a slight angle to the skin and vessel. If intravascular access is needed for more than a brief injection or one-time blood withdrawal, then a catheter typically is inserted.

Figure 6H:
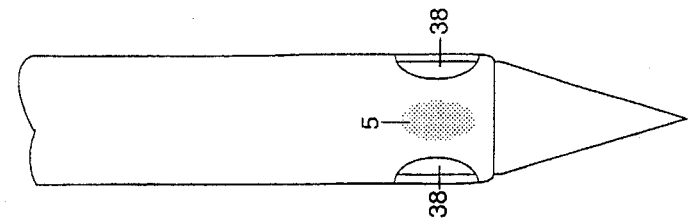
FIGS. 6a–6h show embodiments of needle-catheter combinations including over-the-needle catheters.
Figure 6G:
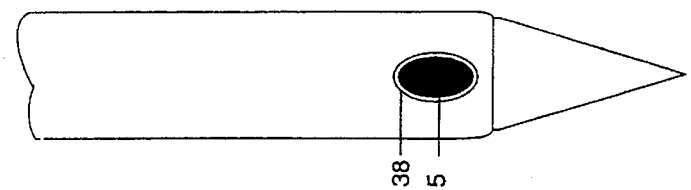
Figure 6F:
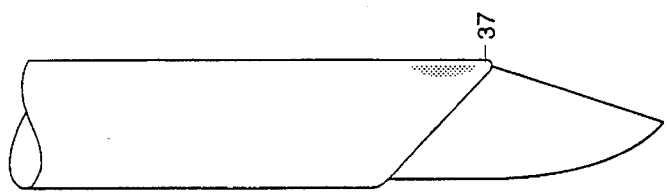
Figure 6E:
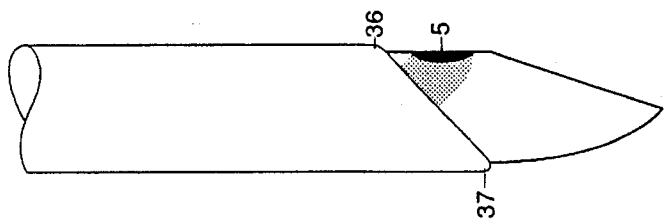
Figure 6D:
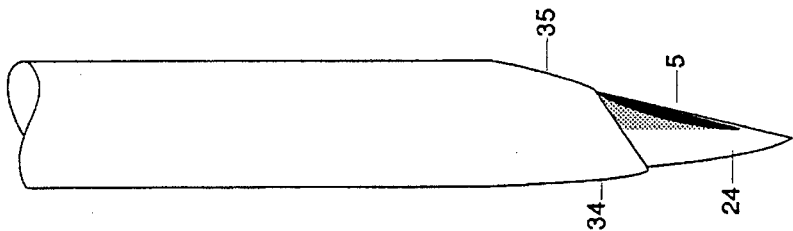
Figure 6C:
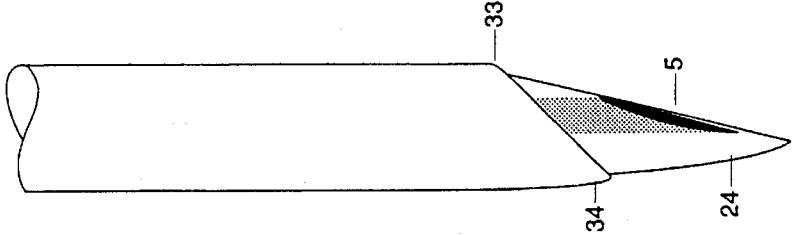

The disclosed methods and apparatus are able to markedly improve the safety and utility of needles and catheter-needle assemblies. In contrast to conventionally employed open-tip needles for intravascular injection, aspiration or catheter placement, the embodiments exemplified in FIGS. 3 and 4 and adapted for catheters in FIGS. 6 and 7 offer the advantages of: (1) increased user safety as a result of decreased inoculum at the site of a sharp point, improved ability to cover the orifices and needle point after use (to be detailed later), and less bedside accumulation of unsuccessful needles; (2) reduced likelihood of vein trauma and coring; (3) increased likelihood that the orifice(s) will be intravascular even if the needle tip has extended beyond the back wall of the vessel; and (4) simplified catheter insertion.

Previously designed hypodermic needles with recessed orifices are ill-suited for intravascular injection and cannulation. Schofield (U.S. Pat. No. 3,181,336) utilized a slit rather than a rounded orifice; this can lead to vessel tearing and infiltration. Hanson (U.S. Pat. No. 2,634,726) utilized a chisel-tip with a single opening on the side of the needle that lies on the distal wall of the vein. Gewecke (U.S. Pat. No. 2,862,495), Morgun (French Patent 1,196,601), Weyl (German Patent 446,818), Galindo (U.S. Pat. No. 4,411,657), and Sprotte (German Patent 3,020,926) introduced needles with points that were suitable for penetration of bottle tips and/or skin but not precise vein penetration. Although adapted for vessel penetration, the invention of Guttman (4,413,993) also differs decidedly from the present disclosure. Guttman adapted the recessed-orifice design to indwelling needles (not needles plus catheters) for intravascular fluid administration, with the expressed goal of minimizing infiltration of fluid which may result from eventual penetration of the vessel wall during long-term needle placement. The Guttman needle has "a sharp point which exhibits a solid circumference extending upstream for a distance equal to at least several diameters of the shaft." This feature may require insertion of a needle to a distance that is greater than that typically required for over-the-needle or through-the-needle catheter insertion. Additionally, its orifice is directed laterally. The disclosed needle series is not limited by such features. We also have introduced other features such as a curved taper into order to optimize intravascular placement and catheter insertion. While the Guttman needle was designed to minimize infiltration if penetration of the distal vessel wall occurred, the curved embodiments of the present series additionally minimize such penetration by minimizing the likelihood that a sharp tip will be pushed against the distal vessel wall.

A. OVER-THE NEEDLE CATHETERS

For purposes of intravascular cannulation, the catheters and needles of the present invention are designed as matched catheter-needle assemblies with the catheter coaxially placed over the needle. This approach is suitable to many of the channel/orifice orientations that are disclosed herein and to other variations that would be apparent to those skilled in the art after reading the information disclosed herein. Proper orientation can be assured by aligning marks on needle and catheter hubs; markings are commonly employed at these sites and are not illustrated in the present disclosure. Several embodiments are illustrated in FIGS. 6a–6h.

Figure 6B:
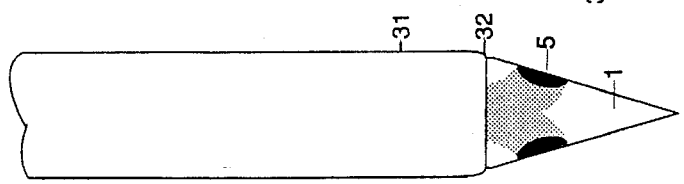
Figure 6A:
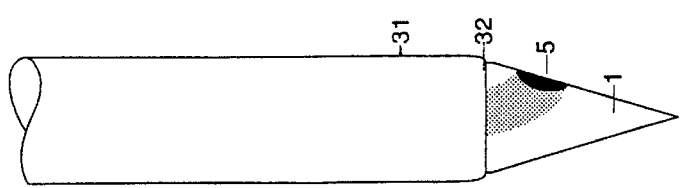
Figure 7:
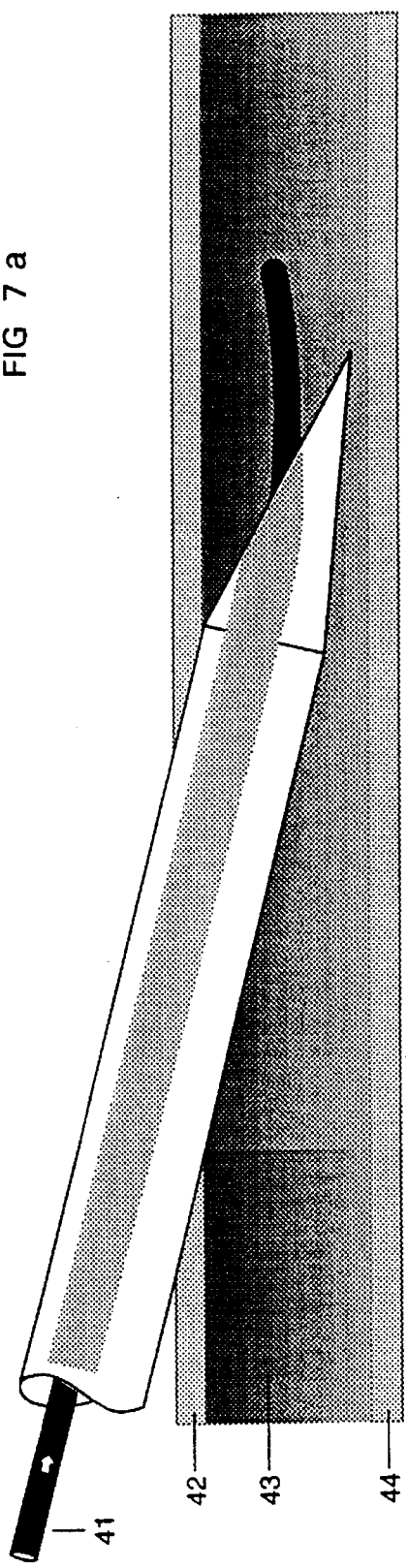
FIGS. 7a and 7b are diagrams illustrating the threading of a through-the-needle guidewire into a blood vessel via needles according to embodiments of the invention.
Figure 7:
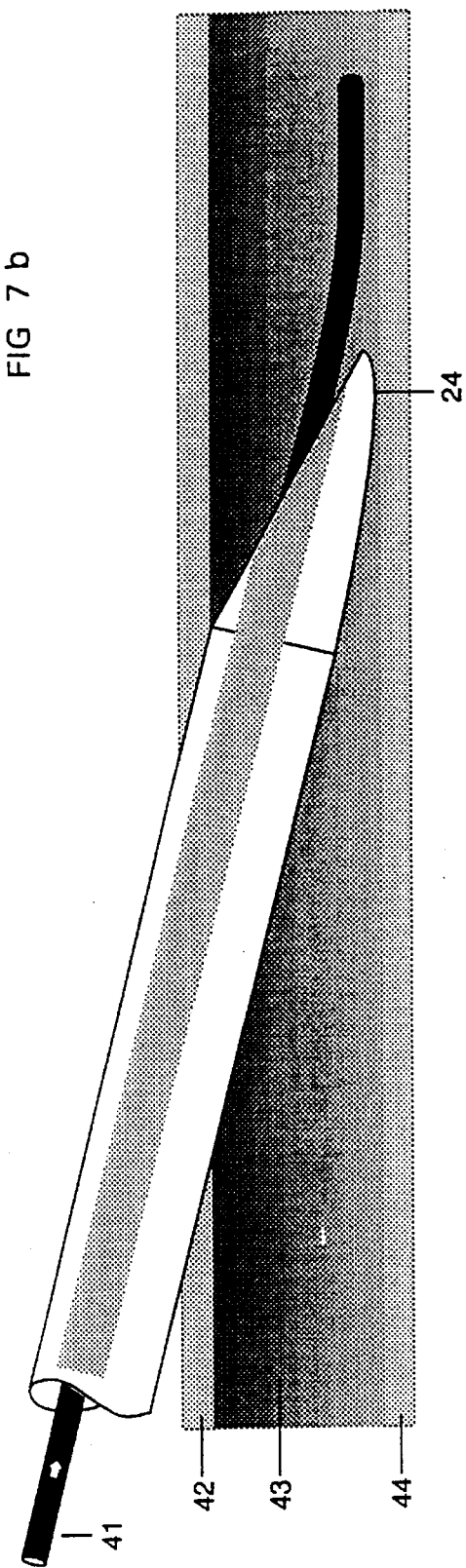

FIG. 6a illustrates the needle-catheter combination with a needle comparable to that detailed in FIG. 3a; a catheter 31 overlies the needle to terminate at a site 32 proximal to the needle orifice 5. It extends along the needle almost to the hub. Although a needle with a single recessed orifice may be used, the presence of more than one orifice decreases the likelihood that the wall of a small or partially collapsed vessel will occlude the needle and prevent detection of flashback. FIG. 6b illustrates a catheter overlying a needle comparable to that illustrated in FIG. 3d.

FIG. 6c illustrates an over-the-needle catheter arrangement for the needle of FIG. 4d. A major advantage of this configuration is that the rounded side 24 of the needle may expand, rather than puncture, the back wall of the vessel. The tip of such a needle is designed so as to maintain a pointedness that is adequate for penetration. The particular embodiment in FIG. 6c includes a catheter whose side 33 ipsilateral to the needle orifice 5 is shortened to a point proximal to the taper, thereby assuring exposure of said orifice 5. On the side contralateral to the needle orifice, the distal end 34 of the catheter is longer in order to facilitate catheter threading.

FIG. 6d illustrates an over-the-needle catheter with an additional feature: the proximity of the needle and catheter is maintained by adding a taper 35 to the end of the catheter which conforms to the taper of the needle proximal to the needle orifice.

The orifices of the needle-catheter assembly need not be located on the taper, nor must they lie distal to the catheter. FIG. 6e illustrates an angled catheter with one side 36 ending proximal to an orifice 5 on the needle shaft. As illustrated in FIG. 6f and detailed later, such embodiments allow deliberate occlusion of the orifice by rotating the long side 37 of the catheter over the needle orifice 5.

An alternative embodiment is shown in FIG. 6g. It entails a matched assembly where the catheter itself is constructed with orifice(s) 38 which overlie(s) the needle orifice(s) 5. FIG. 6h illustrates the effect of catheter rotation (or withdrawal or advancement), namely, occlusion of the needle orifice(s) 5.

Although prior needle series have in general utilized a solid-tipped needle for catheter insertion, the disclosed methods, which increase user safety, and the claimed features, are unique. In 1988, Foran (U.S. Pat. No. 4,767,407) introduced a needle wherein the axial channel narrows to an open end while the remainder of the shaft continues to a solid point. Since the remainder of the shaft extends beyond the orifice, the orifice may be considered recessed. This needle, designed to facilitate catheter insertion into a constricted vein by providing an elongated sharp tip, requires a "triple-bevel" construction. This thereby created a needle of changing width, with a single forward-oriented bevel at a fixed interval from the end of the shaft. The Foran device has clinical disadvantages. The present needle series and methods obtain different objects and offer far greater versatility with respect to design of the tip, taper, and orifices and the relationships among them.

B. THROUGH-THE-NEEDLE CATHETERS, GUIDEWIRES & PROBES

As noted above, a catheter or monitoring probe may be threaded through a needle (as opposed to over-the-needle). Although assemblies for through-the-needle catheter and guidewire insertion are commercially available (e.g., Radial Artery Catheterization Set, Arrow International, Inc.; U.S. Pat. No. 4,417,888), they do not contain the unique features of the inventive needle assemblies. Currently available set-ups consist of a standard open-bevel needle, which lacks the safety of our inventive recessed-orifice needles. Additionally, several embodiments of the inventive series orient the through-the-needle wire so that it may be readily advanced without encountering the distal vessel wall.

FIG. 7a illustrates a needle similar to that of FIG. 3a with a guidewire, needle catheter, or monitoring probe 41 in its channel. The needle tip has pierced the proximal wall 42 of the vessel 43; the catheter is directed to lie in the vessel. FIG. 7b shows a needle similar to that of FIG. 4d. The curved portion 24 of the distal end of the needle expands and protects the remote vessel wall 44, while the axial channel directs the guidewire 41 along the longitudinal axis of the vessel.

An additional advantage of the needles introduced according to this invention is that a narrow needle tip can be used even if a relatively wide guidewire is to be inserted since the orifice required for guidewire passage is recessed from the needle tip.

The aforementioned description of a through-the-needle guidewire also would be applicable to an intravascular monitoring probe or catheter. In addition, the aforementioned description of intravascular procedures also may be applied to safer and more efficient cannulation of neurovascular sheaths, myofascial-planes, etc. and insertion of catheters through diaphragms on bottle tops, IV sideports, etc.

III. MEANS FOR SECURING NEEDLES IN PLACE

In traditional settings, needles remain in situ by a friction fit between the needle shaft and the rubber diaphragm of a bottle top or injection port. Not uncommonly, the attachment is maintained with tape; it remains insecure, with the potential for slippage and disconnection (with subsequent risk of exposure to contaminated needles).

It is particularly important that needles of the present invention remain in situ after puncturing a diaphragm, so that the orifice(s) remains beyond the diaphragm. For such purposes, the needle may be modified on the shaft alone, at the hub-shaft junction, or on the hub alone. As is the case for existing means for securing open-bevel needles, the diaphragm or its casing may be modified to match the needle configuration or adaptors may be interposed to achieve this effect with existing supplies. As illustrated in the figures, the alignment of plastic and rubber may be varied to facilitate the manufacturing process in that plastic, if it is included, may overlie, underlie, or lie within the rubber diaphragm.

As illustrated in FIGS. 8a and 8b, such securement may be obtained by modifying the needle shaft. FIG. 8a shows an embodiment of the invention in which the tip, taper and part of the shaft of a recessed-orifice needle 101a have passed through a diaphragm 102. The threaded portion 103 on the shaft either reduces the likelihood of accidental needle withdrawal after the threading has passed beyond the diaphragm, or improves securement within the diaphragm by frictional engagement (or screwing into female grooves of a matched receptacle). FIG. 8b shows a recessed-orifice needle 101b with tapered flanges 104 which project radially outward proximal to the orifice 105, such that insertion beyond this point and withdrawal (or disconnect) require alignment with corresponding slits in a matched diaphragm. It should be readily apparent to those skilled in the art that securement also may be attained by such means as luer-locking or ribbed engagement.

Figure 9:
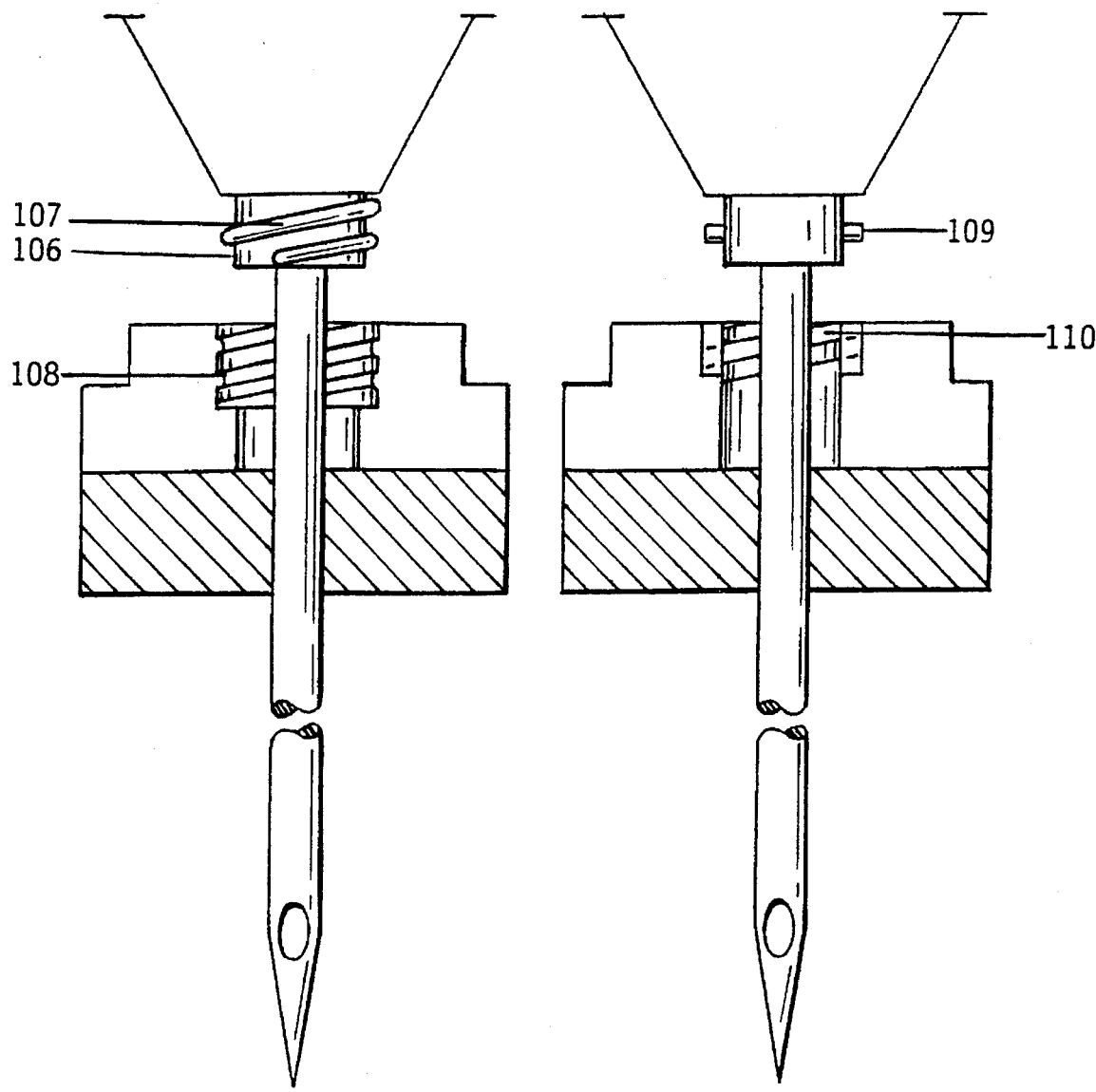
FIGS. 9a and 9b show needle modifications for securement involving the hub-shaft junction.

As illustrated in FIGS. 9a and 9b, securement may be obtained by modifying the hub-shaft junction 106. In FIG. 9a, male threads 107 on the hub-shaft junction 106 form a threaded connection with female threads 108 on the diaphragm casing. In FIG. 9b, a luer-lock connection is made between tabs 109 on the hub-shaft junction 106 and a groove 110 on the diaphragm casing. As noted above, such connections may be accomplished above, below or within the rubber diaphragm.

Figure 10:
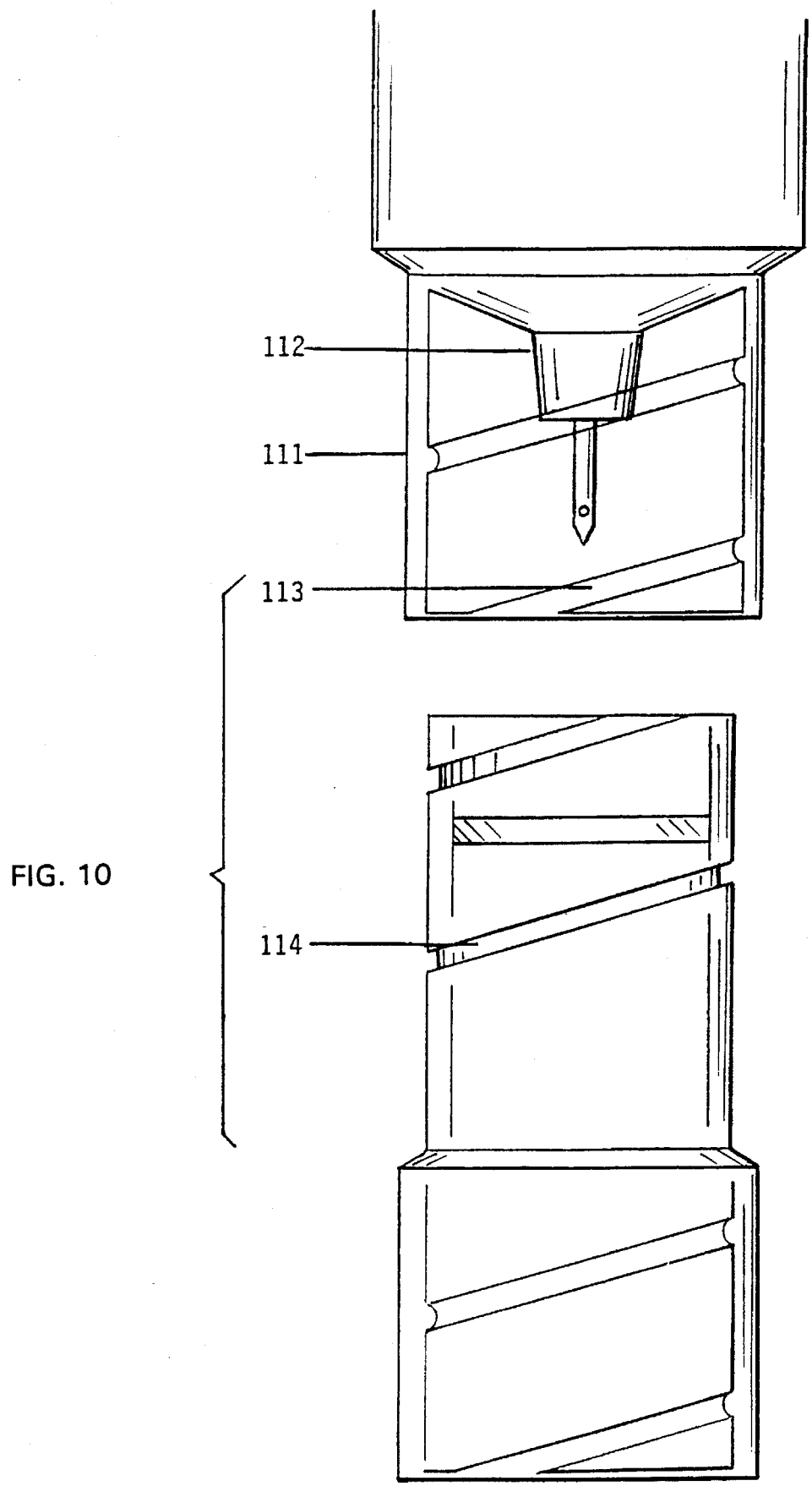
FIG. 10 shows a needle modification for securement involving the hub, with the needle being encased in a housing which engages a receptacle, e.g., a casing of a diaphragm.

Securement may be obtained at the level of the needle hub. The hub of an inventive needle may be encased in a housing which engages a diaphragm by friction, screwing, luer-locking, or ribbed engagement. FIG. 10 illustrates a housing 111 which emanates from the needle hub 112. The housing encases the hub, shaft, and tip of the recessed-orifice needle. In the present embodiment, internal (female) threads 113 on the housing are matched to external (male) threads 114 on the diaphragm for advancement and securement.

IV. MEANS FOR COVERING THE ORIFICES WHEN NOT IN USE

The recessed-orifice needles, as described herein, are uniquely suited for covering and capping when not in use. The solid tip may be covered with a penetrable sheath or cap since it does not cause undesirable coring. Additionally, the recessed orifices may be covered without the need to cover the needle tip and thereby possibly compromise insertion.

Figure 11A:
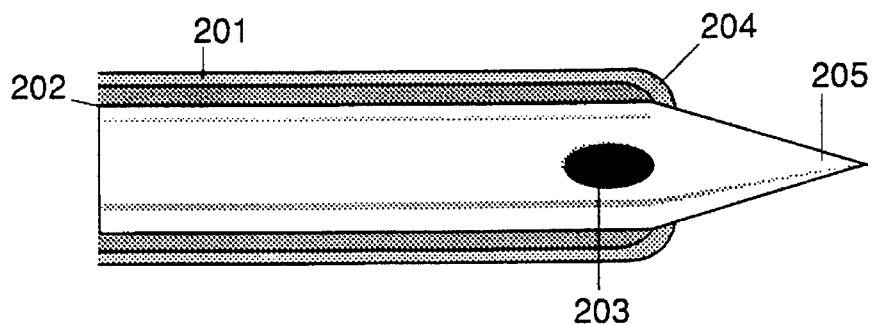
FIGS. 11a–11c show embodiments of retractable sheaths which increase the safety associated with use of the inventive needles, in which the sheath overlies the recessed orifice(s) in its extended state and exposes the orifice in its retracted state.
Figure 11B:
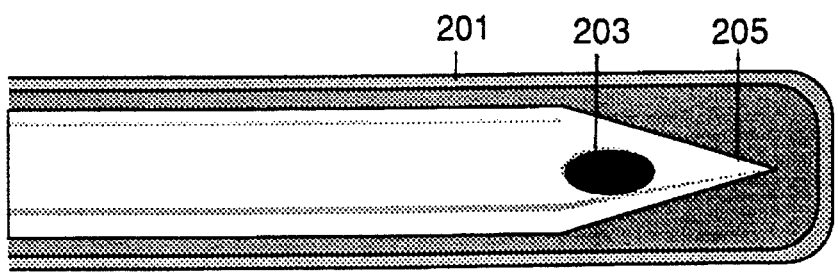

As illustrated in FIG. 11a, one such means is to attach a compressible, resilient (e.g., rubber) sheath 201 which extends from a site 202 proximal to (i.e., hubward of) the orifice(s) 203 to a site 204 between the orifice(s) and the needle tip 205. The sheath may frictionally adhere to the needle and abut the needle hub or it may be secured at its proximal end 202. FIG. 11b illustrates an embodiment where, in the extended position, the sheath 201 extends beyond the solid tip 205.

Figure 11C:
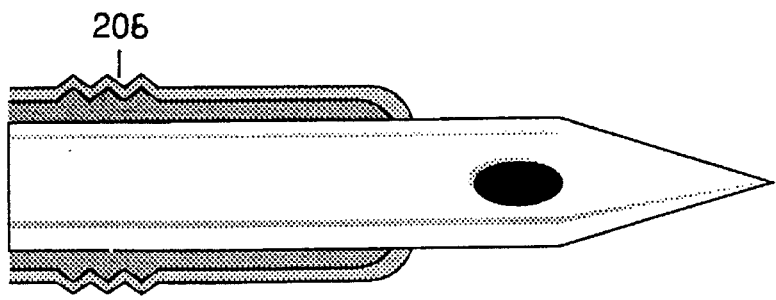

Upon needle entry into a rubber diaphragm or through the skin, the retractable sheath in either of these embodiments is displaced hubward to expose the orifice(s). As illustrated in FIG. 11c, this may be accomplished by compression of a collapsible segment 206; alternatively, the entire sheath may be collapsible in this manner. Upon needle withdrawal, the sheath once again extends to cover the orifices. If deemed indicated, inadvertent collapsing of the sheath may be prevented by a sleeve (not shown) which overlies the collapsible section when the needle is not in use. The sleeve could be slidably displaced and secured with the means detailed above for needle securement and detailed below for needle caps.

Figure 12:
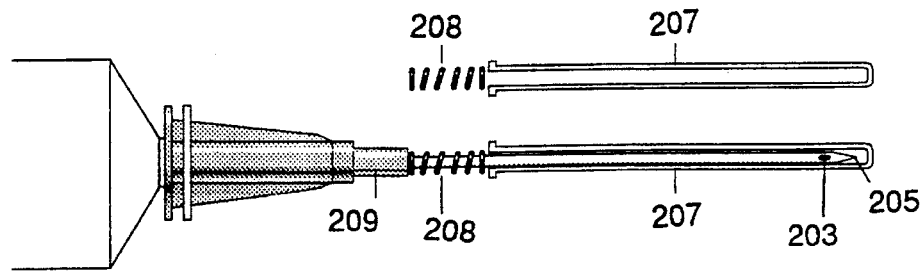
FIGS. 12a–12c illustrate recessed-orifice needles with retractable sheaths which are maintained in position by a proximally located spring.
Figure 12:
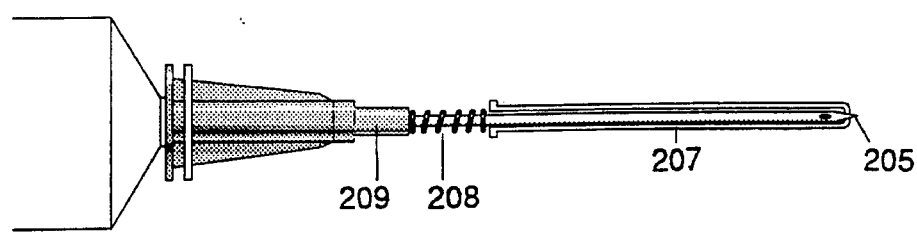
Figure 12:
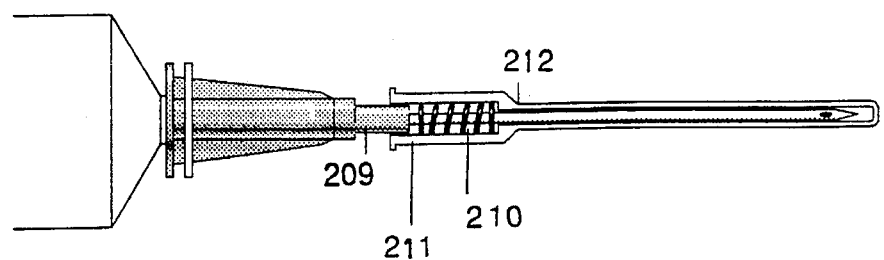

As illustrated in FIGS. 12a–12c, inventive needles also may be covered by a sheath (collapsible or noncollapsible) that is maintained in position by a proximal spring. FIG. 12a illustrates a sheath 207 extending beyond the needle tip 205 and a spring 208 abutting the needle hub 209. FIG. 12b shows a sheath 207 ending between the needle orifice 203 and tip 205 in its extended position. The spring may be secured to the needle shaft or hub or simply abut the hub. Upon entry of the needle tip into a patient or receptacle, the sheath is displaced and/or compressed against the spring to expose the orifice(s); upon needle removal, the spring restores the sheath to its normal position.

FIG. 12c illustrates an embodiment wherein a spring 210 is incorporated with the proximal end 211 of a modified sheath 212. The proximal end of the sheath may attach to the needle at the hub-shaft junction 209 by such means as frictional engagement, ribbed engagement, luer-locking, or screwing.

The retractable sheath of the present invention is unlike that provided by Becton-Dickinson for the end of its Vacutainer needle that penetrates the blood-collecting tube. The typical Becton-Dickinson sheath covers the entire tip of an open-bevel needle and is not designed for the end of a needle that penetrates the skin; nor is it usable in a method of reducing the risk of disease transmission. It minimizes leakage of blood or entrainment of air when the opposite end of the needle is within a blood vessel; in contrast to many of the uses proposed for the inventive series, coring would be acceptable in this particular setting. The retractable sheath of the present invention also differs from that proposed by Alchas in 1985 (U.S. Pat. No. 4,537,593). In the Alchas disclosure, a sleeve is maintained on the needle shaft to allow gases to be vented by passing freely between the shaft and the inside diameter of the sleeve.

An alternate safety feature and method according to the present invention includes a nonretracting sheath or overlying catheter that may be rotated or otherwise adjusted to expose orifices during use but otherwise allow them to be covered. This would not only reduce the healthcare worker's exposure to a used needle but also would enable one to prevent leakage once flashback has been confirmed. One embodiment is illustrated by FIGS. 6g and 6h; it entails a catheter with orifices that may be aligned with respect to those of the needle. A second embodiment is shown in FIGS. 6e and 6f; here, rotation causes the longer edge of the catheter to overlie the needle orifice. The catheter or sheath may simply be turned by a fixed degree; the turning angle may be limited by one or more protrusions on the needle hub which project through a slit on the catheter hub (or vice versa). As illustrated and described above in connection with needle securement, the outside of the needle hub, shaft or hub-shaft junction and the inside of the corresponding portion of the cover also may be matched for securement by friction, screwing, luer-locking or a detent for clicking into place. Alternatively, a matched stylet may be inserted to occlude flow, but the inclusion of a stylet does not offer the simplicity of rotating an over-the-needle catheter which already is in place.

The aforementioned forms of covering the needle orifice(s) may be accomplished in a variety of ways, many of which simply entail combining features described in different sections of this disclosure. Others likewise would be apparent to those skilled in the art after reading the descriptions provided herein.

V. MEANS FOR CAPPING, UNCAPPING AND RECAPPING

Capping of contaminated needles is considered to be so dangerous to the healthcare worker that many experts have recommended that the procedure be abandoned. Unfortunately, the alternatives (e.g., carrying exposed needles to the disposal box) have not proved to be significantly safer. While the solid tip configuration of the present invention should decrease the infectivity of a given needle stick, the configuration alone does not prevent such a stick. However, the solid tip is uniquely suited for new capping procedures. The solid needle tip allows a penetrable cover to be placed over it without risk of coring (with subsequent risk of contamination to the patient) upon penetration by the needle point. In contaminated settings, the penetrable cap can be used with both hands remaining behind the needle point and thus at far less risk of being stuck. The entire cap may be made of the same penetrable material (e.g. rubber); it may contain plastic reinforcements to provide a cap-like configuration; or more standard caps may be modified with a penetrable diaphragm at their tips.

Figure 13:
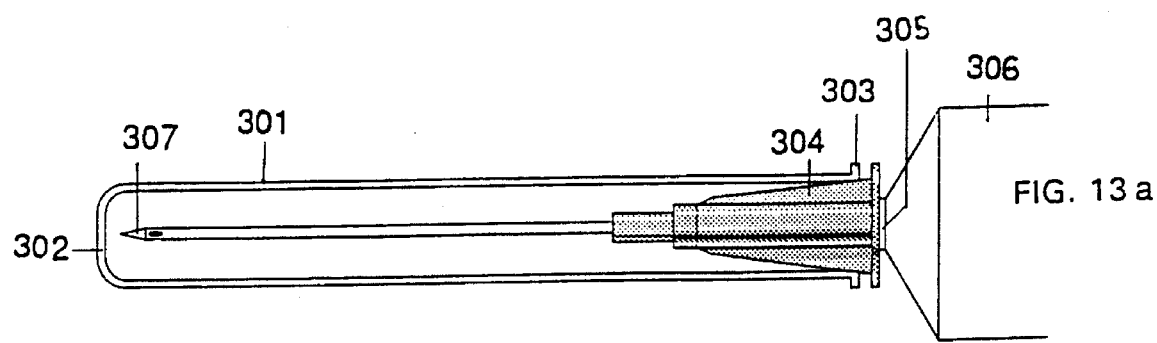
FIGS. 13a–13d show respective embodiments of needle caps according to the present invention, including a penetrable distal end, a means of compressing the cap in order to permit exposure of the needle tip, and a sleeve to prevent exposure from occurring inadvertently.
Figure 13:
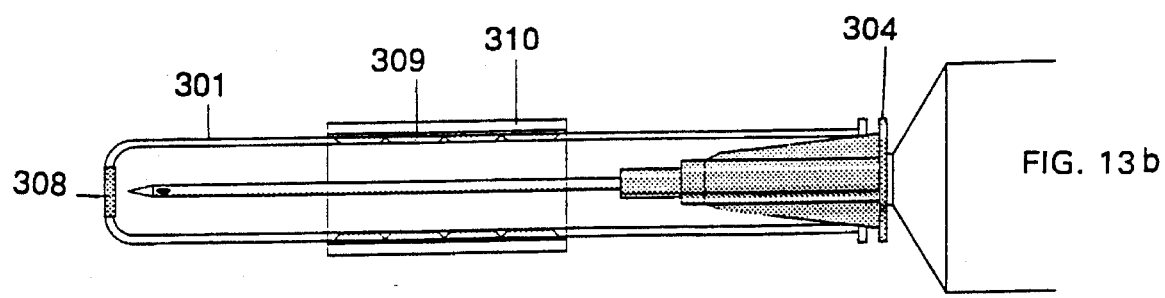
Figure 13:
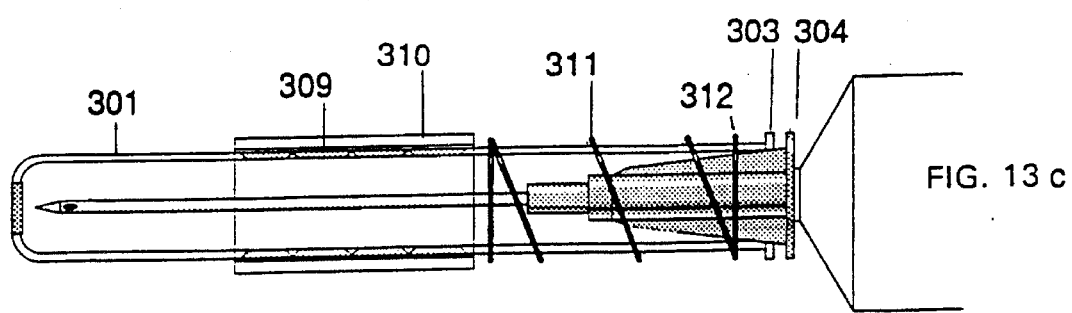
Figure 13:
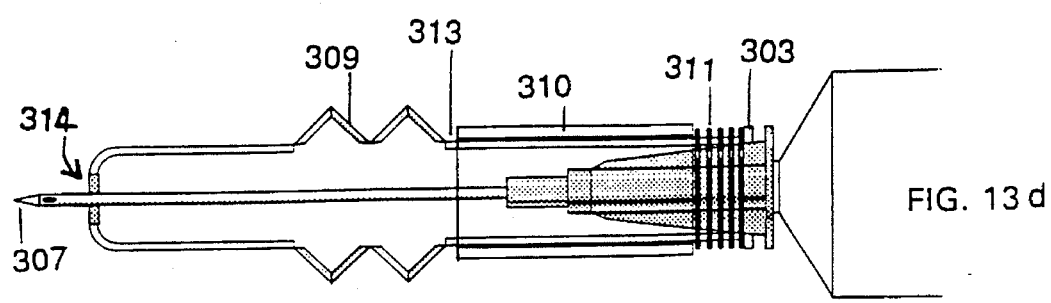

FIG. 13a illustrates a combination of an inventive needle and a conventional needle cap 301 with a solid tip 302. It is shown here with its proximal end 303 attached to the needle hub 304 with the conventional friction fit. The hub has a standard opening 305 for attachment of a syringe 306 or intravenous tubing. Distally, the cap encloses the needle tip 307.

FIG. 13b illustrates a modification of the conventional cap according to the present invention. The cap has a penetrable tip (e.g. rubber diaphragm) 308, a collapsible section (e.g. bellows or spring) 309, and an overlying sleeve 310. When covered by the sleeve 310, the collapsible section 309 cannot collapse because of the sleeve 310. The sleeve may be kept in place by such means as friction, an overlying ring or previously described means of securement such as ribbed engagement, screwing or luer-locking between the inner surface of an end of the sleeve and the outer wall of the cap.

FIG. 13c includes a spring 311, which may be anchored to a site 312 at or near the proximal end 303 of the cap. As illustrated in FIG. 13d, when one wishes to expose the needle point 307 and orifice(s), the sleeve 310 is displaced to a position 313 hubward of the collapsible segment 309. This permits the cap to be withdrawn to a location 314 behind to the orifice(s) as the collapsible segment 309 becomes folded. Once retracted, the sleeve could be managed in a number of ways. It is shown here being maintained against a compressed spring 311. Once pressure against this spring is released, the spring would urge the sleeve forward. Alternatively, the sleeve may be allowed to slide freely between the collapsed segment 309 and the proximal end 303 of the cap or the sleeve may be maintained in position by such previously described means as friction, snap-fit, luer-locking or screwing to the proximal needle cap or needle hub. Alternatively, the retracted cap itself could be secured by these means. As an alternative to the collapsible segment 309, one could provide for cap shortening with a displaceable or telescoping segment.

Figure 14:
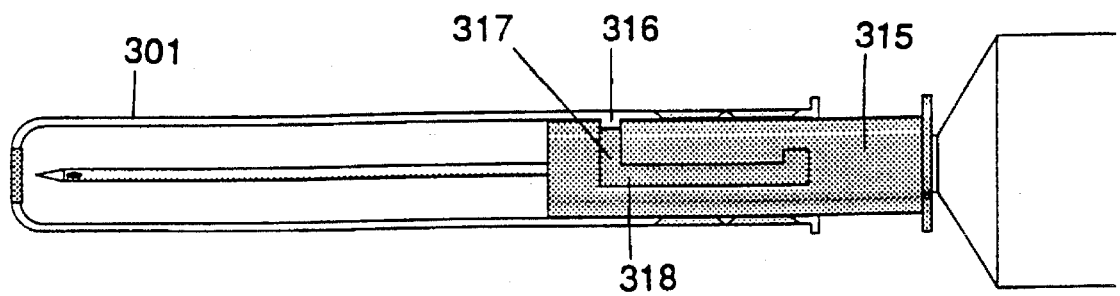
FIGS. 14a and 14b show an alternate means of withdrawing the needle cap and securing it in place.
Figure 14:
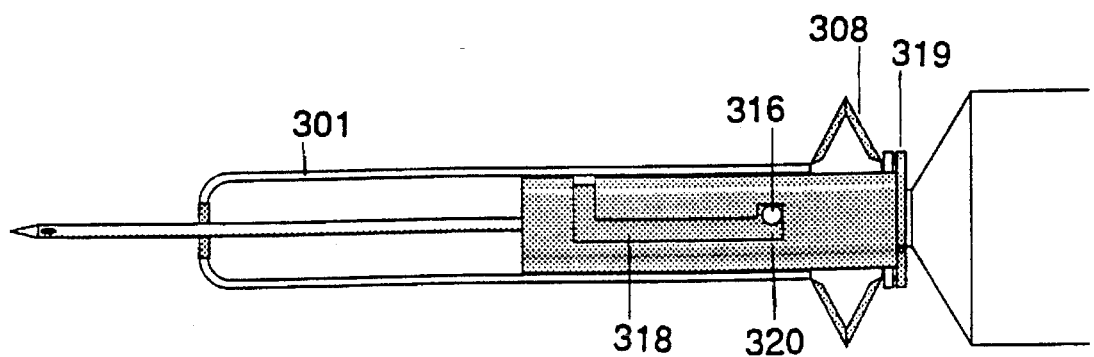

FIGS. 14a and 14b illustrate alternative means of cap 301 withdrawal. In this embodiment, substantially the entire cap is withdrawn, with its proximal end being withdrawn over the needle hub which in this embodiment is a specially designed elongated needle hub 315. FIG. 14a is a lateral view which shows a locking tab 316 on the inside of the cap 301. The locking tab 316 engages the distal end 317 of a groove 318 in the elongated needle hub 315. In the present embodiment the needle hub 315 is of uniform diameter in order to facilitate the groove alignment. For illustrative purposes, the groove 318 has been located near the midportion of the needle hub 315. The groove may be located more proximally and thereby obviate the need for such a long hub.

FIG. 14b is a top view wherein the cap 301 has been withdrawn such it abuts the proximal end 319 of the elongated needle hub. This has resulted in the tab 316 lockingly engaging the proximal end 320 of the groove 318 in the needle hub, and the needle being exposed.

An alternative embodiment (not shown) would entail a tab on the hub and a groove in the cap. As previously illustrated, retraction also could be accomplished by such means as screwing, friction, and ribbed engagement.

Figure 15:
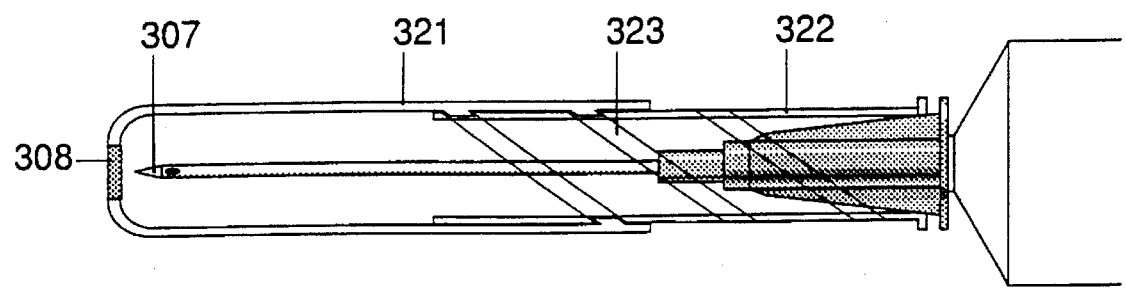
FIGS. 15a and 15b show respective additional embodiments of a penetrable needle cap.
Figure 15:
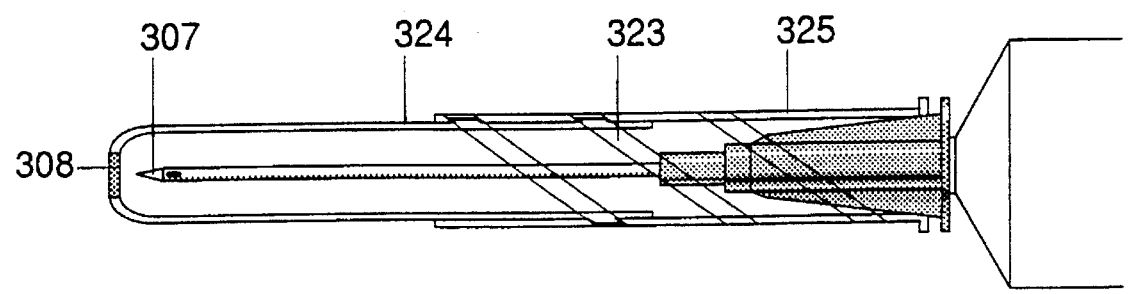

FIGS. 15a and 15b illustrate alternative embodiments wherein the cap itself is structured such that the distal section may override the proximal section or vice versa. FIG. 15a illustrates a distal section 321 which is wider than the proximal section 322. To expose the needle through the rubber diaphragm 308 at the distal end of the cap, the tip 308 may be placed against the surface to be penetrated and the needle then may be advanced such that its tip penetrates the surface. Alternatively, the distal section may first be withdrawn over the proximal section prior to contacting the surface to be penetrated. In the embodiment illustrated, grooves 323 provide threaded connection between the inner surface of the distal cap and the outer surface of the proximal cap. As illustrated and described above, alternate means for withdrawal and securement include, friction, ribbed engagement and luer-locking. Again, a collapsible segment or a retaining spring may be included. FIG. 14b illustrates an embodiment wherein a narrowed distal section 324 of the cap fits within a wider proximal section 325.

In addition to minimizing the need to place one's hand in front of a used needle during capping, the configurations illustrated in FIGS. 13a–15b also have the added feature of limiting depth of penetration. The needle cannot be advanced beyond the point at which it maximally emerges from the retracted cap. In addition, the cap is well-suited for inclusion of an antiseptic or germicidal pad at the point of contact. To assure coverage during needle disposal and to allow the healthcare worker to employ a traditional capping procedure if so desired, the cap's penetrable tip may be covered with an outer cap. The outer cap could simply cover the tip or could completely cover the needle-cap assembly as illustrated in FIGS. 13a–15b. The outer cap could be applied and removed in the traditional manner. It could be secured by friction or the other means illustrated above. If one were willing to incur the expense and the limitations associated with matched syringes and needles (or matched intravenous tubing and needles), then the aforementioned modifications may readily be adapted to allow withdrawal of a needle cap over the barrel of a syringe (or the end of intravenous tubing) and thereby allow even greater degrees of needle tip exposure and improved needle-syringe or needle-tubing securement. Other embodiments, which would be logical extensions of those introduced in FIGS. 13a–15b and should be readily apparent to those skilled in the art who have read this disclosure, are considered to be included within the scope of the invention.

Although the present invention has been described in relation to particular embodiments thereof, many other variations and modifications and other uses will become apparent to those skilled in the art. All such variations and equivalents of the disclosure are considered to be within the fair spirit and scope of the claimed invention.

What is claimed is:

1. A hypodermic needle adapted for reducing the risk of infection from material in a used hypodermic needle, comprising:

a needle shaft having a bore; a solid tip with no orifice at a distal end of said needle shaft;

at least one outlet orifice which communicates with said bore, for passage of all material into and out of said needle, said orifice being formed in said needle at a lateral position spaced back from said solid tip by an amount sufficient to reduce the risk that an individual who contacts said tip of said needle will contact material retained in said at least one outlet orifice of said needle; and cover means located on said needle shaft and being operable from a location remote from said tip and said orifice for selectively. exposing and blocking said orifice, said cover means surrounding and being rotatable about said needle to cover said orifice when said cover means is located in a first position and to expose said orifice when said cover means is located in a second position; wherein the cover means comprises a sheath having an aperture which can be aligned with said orifice to expose said orifice and has a solid portion which can be aligned with said orifice to block said orifice.

2. A hypodermic needle adapted for reducing the risk of infection from material in a used hypodermic needle, comprising:

a needle shaft having a bore; a solid tip with no orifice at a distal end of said needle shaft;

at least one outlet orifice which communicates with said bore, for passage of all material into and out of said needle, said orifice being formed in said needle at a lateral position spaced back from said solid tip by an amount sufficient to reduce the risk that an individual who contacts said tip of said needle will contact material retained in said at least one outlet orifice of said needle; and cover means located on said needle shaft and being operable from a location remote from said tip and said orifice for selectively exposing and blocking said orifice, said cover means surrounding and being rotatable about said needle to cover said orifice when said cover means is located in a first position and to expose said orifice when said cover means is located in a second position; wherein the cover means comprises a sheath having a longer edge portion which blocks said orifice when rotated to be aligned with said orifice and a shorter edge portion which exposes said orifice when rotated to be aligned with said orifice.

3. A sheath for a needle, the needle having a hub and a solid tip with no orifice at a distal end thereof, at least one longitudinal bore which terminates proximal to said needle tip, at least one outlet orifice in communication with said bore for passage of all material into or out of said needle, wherein said outlet orifice is located at a lateral position spaced back from said solid tip by an amount sufficient to reduce the risk that an individual who contacts said tip of said needle will contact material retained in said at least one outlet orifice of said needle, the sheath comprising:

a sheath body having a substantially circular shape for fitting over and engaging the hub of the needle, the sheath body being rotatable about the needle so that the sheath body can be aligned with the needle orifice to cover and expose the needle orifice; wherein said sheath body is formed so as to be operable from a location remote from the needle tip and the needle orifice for selectively exposing and blocking the needle orifice with the sheath; and the sheath body has an aperture formed therein which can be aligned with said orifice to expose said orifice and has a solid portion which can be aligned with said orifice to block said orifice.

4. A sheath for a needle, the needle having a hub and a solid tip with no orifice at a distal end thereof, at least one longitudinal bore which terminates proximal to said needle tip, at least one outlet orifice in communication with said bore for passage of all material into or out of said needle, wherein said outlet orifice is located at a lateral position spaced back from said solid tip by an amount sufficient to reduce the risk that an individual who contacts said tip of said needle will contact material retained in said at least one outlet orifice of said needle, the sheath comprising:

a sheath body having a substantially circular shape for fitting over and engaging the hub of the needle, the sheath body being rotatable about the needle so that the sheath body can be aligned with the needle orifice to cover and expose the needle orifice; wherein said sheath body is formed so as to be operable from a location remote from the needle tip and the needle orifice for selectively exposing and blocking the needle orifice with the sheath; and the sheath has a longer edge portion which blocks said orifice when rotated to be aligned with said orifice and a shorter edge portion which exposes said orifice when rotated to be aligned with said orifice.

* * * * *

UNITED STATES PATENT AND TRADEMARK OFFICE
CERTIFICATE OF CORRECTION

PATENT NO. : 5,478,328

DATED : December 26, 1995

INVENTOR(S) : David G. Silverman, et al.

It is certified that error appears in the above-identified patent and that said Letters Patent is hereby corrected as shown below:

Column 4, following line 2, insert Table 1, attached hereto.

Signed and Sealed this

Seventeenth Day of October, 2000

Attest:

Q. TODD DICKINSON

*Attesting Officer*  *Director of Patents and Trademarks*

TABLE 1

NEEDLE REQUIREMENTS IN VARIOUS SETTINGS

| USE | POINT | IS OPEN TIP NEEDED?[1] | IS EXPOSED TIP NEEDED?[2] |
|---|---|---|---|
| A. Insertion Through the Skin | | | |
| intravenous injection | sharp[3] | no | yes |
| intramuscular injection | sharp | maybe | yes |
| subcutaneous injection | sharp | no | yes |
| blood sampling | sharp | no | yes |
| needle as guide for catheter insertion | sharp | no | yes |
| B. Insertion Into Rubber Diaphragm of Bottle or Bag[4] | | | |
| single puncture | tapered | no | maybe[5] |
| multiple punctures | tapered or sl. sharp | no | maybe[5] |
| C. Insertion Into Rubber Sideport of Intravenous (i.v.) Tubing[6] | | | |
| single injection | tapered | no | no[7] |
| continuous infusion | tapered | no | no |
| multiple injections | tapered or sl. sharp | no | no |

---

1 = i.e., is it unacceptable for orifices to be recessed?

2 = i.e., is it unacceptable for the needle to be recessed in a plastic casing and/or possibly eliminated through use of matched cannula and receptor?

3 = definite hazard to a healthcare worker after it has contacted a patient.

4 = may be a source of contamination to a healthcare worker if bottle or bag contains blood or products for administration to a patient or if it has been contaminated by previous needle insertion.

5 = in many settings, a recessed needle would not have access to the diaphragm (which may be flush to the bag or bottle) unless a special configuration or adaptor is employed.

6 = may be a source of contamination to a healthcare worker if there has been some backflow through the tubing from the patient (not uncommon) or if a contaminated product was administered previously via the i.v. tubing and/or the injection site.

7 = the diaphragm of sideport typically is not flush to the tubing; hence, there is room for casing around the needle if one wishes to employ such a configuration.